United States Patent
Okaguchi et al.

(10) Patent No.: US 8,658,097 B2
(45) Date of Patent: Feb. 25, 2014

(54) SENSOR FOR DETECTING SUBSTANCE IN LIQUID

(75) Inventors: Kenjiro Okaguchi, Moriyama (JP); Takuo Hada, Nagaokakyo (JP); Michio Kadota, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 591 days.

(21) Appl. No.: 12/273,569

(22) Filed: Nov. 19, 2008

(65) Prior Publication Data

US 2009/0060790 A1    Mar. 5, 2009

Related U.S. Application Data

(63) Continuation of application No. PCT/JP2007/061428, filed on Jun. 6, 2007.

(30) Foreign Application Priority Data

Jun. 16, 2006    (JP) .................................. 2006-167302

(51) Int. Cl.
*G01N 15/06* (2006.01)
*G01N 21/75* (2006.01)

(52) U.S. Cl.
USPC .......................................... 422/68.1; 422/402

(58) Field of Classification Search
USPC .................................................. 422/58, 68.1
See application file for complete search history.

(56) References Cited

U.S. PATENT DOCUMENTS

| | | | |
|---|---|---|---|
| 4,895,017 A * | 1/1990 | Pyke et al. .................... | 73/24.06 |
| 5,306,644 A | 4/1994 | Myerholtz et al. | |
| 7,389,673 B2 | 6/2008 | Kimura et al. | |
| 2007/0107516 A1 * | 5/2007 | Fujimoto et al. ................ | 73/579 |
| 2010/0058834 A1 * | 3/2010 | Cobianu et al. .............. | 73/24.01 |

FOREIGN PATENT DOCUMENTS

| | | |
|---|---|---|
| EP | 1788384 A1 * | 5/2007 |
| JP | 03-140838 A | 6/1991 |
| JP | 05-322736 A | 12/1993 |
| JP | 3481298 B2 | 12/2003 |
| JP | 3488554 B2 | 1/2004 |
| JP | 2004-340766 A | 12/2004 |
| WO | 2005/003752 A1 | 1/2005 |

(Continued)

OTHER PUBLICATIONS

Machine translated version of WO 2006/027893.*

(Continued)

*Primary Examiner* — Dean Kwak
(74) *Attorney, Agent, or Firm* — Keating & Bennett, LLP

(57) ABSTRACT

A sensor for detecting a substance in liquid includes a sensing circuit including a sensing surface acoustic wave (SAW) element in which a reaction film to react with a substance in liquid, a reference circuit including a reference SAW element including an IDT and not including a reaction film, a first signal source driving the sensing circuit, a second signal source driving the reference circuit and being independent of the first signal source, and a differential circuit arranged to output a differential output between an output of the sensing circuit and an output of the reference circuit. The frequency of a first frequency signal output from the first signal source is different from the frequency of a second frequency signal output from the second signal source, thereby making a driving frequency for the sensing SAW element and a driving frequency for the reference SAW element substantially the same as or different from one another.

4 Claims, 2 Drawing Sheets

(56) References Cited

FOREIGN PATENT DOCUMENTS

WO 2006/027893 A1 3/2006
WO 2006/027945 A1 3/2006
WO WO 2006027893 A1 * 3/2006

OTHER PUBLICATIONS

Official Communication issued in International Patent Application No. PCT/JP2007/061428, mailed on Oct. 2, 2007.
Okaguchi et al.; "Method for Detecting Substance in Liquid and Sensor for Detecting Substance in Liquid"; U.S. Appl. No. 12/273,571, filed Nov. 19, 2008.
Okaguchi et al.; "Sensor for Detecting Substance in Liquid"; U.S. Appl. No. 12/273,657, filed Nov. 19, 2008.
Official Communication issued in corresponding Japanese Patent Application No. 2008-521161, mailed on May 10, 2011.
Kondoh et al., "Identification of Liquid Samples Using SH-Saw Sensors", The Transactions of the Institute of Electronics, Information and Communication Engineers, The Institute of Electronics, Information and Communication Engineers, vol. J78-C2, No. 1, 1995, pp. 54-61.
Shiokawa et al., "Surface Acoustic Wave Sensor for Liquid-Phase Application", 1999 IEEE Ultrasonics Symposium, vol. 1, 1999, pp. 445-452.

* cited by examiner

SENSOR FOR DETECTING SUBSTANCE IN LIQUID

BACKGROUND OF THE INVENTION

1. Field of the Invention

The present invention relates to sensors for detecting a substance in liquid using a surface acoustic wave element (SAW element), and more specifically, to a sensor for detecting a substance in liquid, the sensor including a sensing SAW element and a reference SAW element.

2. Description of the Related Art

Various sensors have been developed for detecting a substance (detection-target substance) in liquid, for example, a protein. For example, WO2006/027893A1 discloses a sensor for detecting a substance in liquid using a surface acoustic wave element. FIG. 5A is a plan view for describing a sensor for detecting a substance in liquid described in WO2006/027893A1, and FIG. 5B is a front cross-sectional view that illustrates a main portion thereof.

A sensor 101 for detecting a substance in liquid includes a base substrate 102. The base substrate 102 includes an upper surface 102a in which recesses 102c and 102d are provided at locations spaced from a first end 102b. A sensing SAW element 104 and a reference SAW element 105 are disposed in the recesses 102c and 102d, respectively. A resin layer 103 having holes 103b and 103c facing the recesses 102c and 102d, respectively, is laminated on the base substrate 102.

The sensing SAW element 104 includes a piezoelectric substrate, an interdigital transducer (IDT) provided on the piezoelectric substrate, and a reaction film arranged so as to cover the IDT. The reaction film is made of a material that reacts with a detection-target substance in liquid and is coupled to the detection-target substance. The reference SAW element 105 includes an IDT that is provided on a piezoelectric substrate. The reference SAW element 105 does not include a reaction film.

In use, at least the portions in which the holes 103b and 103c are disposed are placed in liquid, and as a result, the reaction film of the sensing SAW element 104 reacts with and couples to a detection-target substance. Accordingly, in the sensing SAW element 104, a mass on the portion in which the IDT is disposed is increased by the coupling to the detection-target substance. In contrast, in the reference SAW element 105, because the reaction film which reacts with the detection-target substance is not provided, there is no increase of mass caused by the coupling to the detection-target substance.

In the sensor 101 for detecting a substance in liquid described in WO2006/027893A1, a change in the speed of sound of a surface acoustic wave caused by an addition of mass in the sensing SAW element 104 is detected as a change in an electrical signal. In this case, the detection-target substance can be detected with relatively high precision by determining the difference between an output from the sensing SAW element and an output from the reference SAW element.

A similar sensor for detecting a substance in liquid is also disclosed in WO2006/027945A1.

As described above, the sensor 101 for detecting a substance in liquid detects the presence or absence and the density of a protein in liquid using the difference between an output signal from the sensing SAW element 104 and that from the reference SAW element 105. Specifically, the difference between an oscillation frequency of an oscillation circuit including the sensing SAW element and that of an oscillation circuit including the reference SAW element is determined in order to detect the presence or absence or the density of the detection-target substance.

In the sensor 101 for detecting a substance in liquid, it is highly desirable that, when the detection-target substance is not present, the characteristic of the sensing SAW element 104 and that of the reference SAW element 105 be substantially the same or approximately equal.

However, when the detection-target substance comes into contact with the SAW elements 104 and 105, the difference between the oscillation frequency of the oscillation circuit including the sensing SAW element 104 and that including the reference SAW element 105 may be relatively small. In such a case, both oscillations may be electromagnetically coupled, and both of the oscillation frequencies may be substantially or exactly the same. For this reason, the difference in frequency between the oscillation circuit including the reference SAW element and the oscillation circuit including the sensing SAW element is approximately zero, such that it is difficult to reliably detect the detection-target substance in liquid with high precision.

SUMMARY OF THE INVENTION

To overcome the problems described above, preferred embodiments of the present invention provide a sensor for detecting a substance in liquid, the sensor being capable of detecting a detection-target substance in liquid with increased sensitivity.

According to a preferred embodiment of the present invention, a sensor for detecting a substance in liquid includes a sensing circuit, a reference circuit, a first signal source, a second signal source, and a differential circuit. The sensing circuit includes a sensing surface acoustic wave (SAW) element. The sensing SAW element includes a piezoelectric substrate, an interdigital transducer (IDT) disposed on the piezoelectric substrate, and a sensing portion in which a reaction film is arranged so as to cover the IDT and react with a detection-target substance in liquid. The reference circuit includes a reference SAW element. The reference SAW element includes a piezoelectric substrate and an IDT disposed on the piezoelectric substrate and having no reaction film arranged so as to cover the IDT. The first signal source drives the sensing circuit. The second signal source drives the reference circuit and is provided independently of the first signal source. The differential circuit is connected to the sensing circuit and the reference circuit and outputs a differential output between an output of the sensing circuit and an output of the reference circuit. The first signal source is arranged to output a first frequency signal, and the second signal source is arranged to output a second frequency signal having a frequency that is different from a frequency of the first frequency signal, thereby providing a driving frequency for the sensing SAW element and a driving frequency for the reference SAW element different.

In the sensor for detecting a substance in liquid according to this preferred embodiment of the present invention, the first and second frequency signals may preferably be selected so as to satisfy dP≥0, for example, where dP=Pr−Ps, wherein Ps is an output signal of the sensing circuit, Pr is an output signal of the reference circuit, and dP is an output signal of the differential circuit. In this case, because the first and second frequency signals are selected so as to satisfy dP≥0, the output of the sensing circuit including the sensing SAW element based on the amplitude of the SAW element caused by the reaction of the detection-target substance in liquid reacts with the reaction film and the addition of mass on the sensing SAW element is relatively low. Accordingly, the magnitude of the output dP from the differential circuit enables the presence or absence and the density of the detection-target substance in liquid to be detected with greater precision and reliability.

Preferably, a 30° to 40° rotated Y-plate X-propagation lithium tantalate (LiTaO$_3$) substrate may be used as the piezoelectric substrate, for example. This enables the detection-target substance in liquid to be detected with greater sensitivity and reliability.

Each of the sensing SAW element and the reference SAW element can be defined by a SAW element that utilizes various surface acoustic waves. Preferably, a SAW element that utilizes surface acoustic waves primarily including shear-horizontal (SH) waves may be used. In this case, each of the sensing SAW element and the reference SAW element can be defined by an end-surface-reflection SAW element. Accordingly, the size of the sensing SAW element and the reference SAW element can be reduced.

In preferred embodiments of the present invention, the sensing SAW element and the reference SAW element are preferably driven by first and second frequency signals, respectively, that are either the same as or different from one another. The differential amplifying circuit outputs a differential output between the output of the sensing circuit including the sensing SAW element based on the amplitude level of the sensing SAW element and the output of the reference circuit including the reference SAW element based on the amplitude of the reference SAW element. Accordingly, the differential output enables the presence or absence or the density of the detection-target substance to be detected based on a decrease in the amplitude level based on a decrease in frequency caused by an increased mass in the sensing SAW element occurring when the detection-target substance is coupled thereto. That is, without an oscillation circuit, the detection-target substance is detected based on the difference in amplitude between the sensing SAW element and the reference SAW element. Accordingly, a driving difference and a decrease in the measurement accuracy do not occur. Thus, the detection-target substance can be detected with greater precision and greater sensitivity.

Other features, elements, steps, characteristics and advantages of the present invention will become more apparent from the following detailed description of preferred embodiments of the present invention with reference to the attached drawings

DETAILED DESCRIPTION OF PREFERRED EMBODIMENTS

Preferred embodiments of the present invention will be described below with reference to the drawings.

Figure 1:
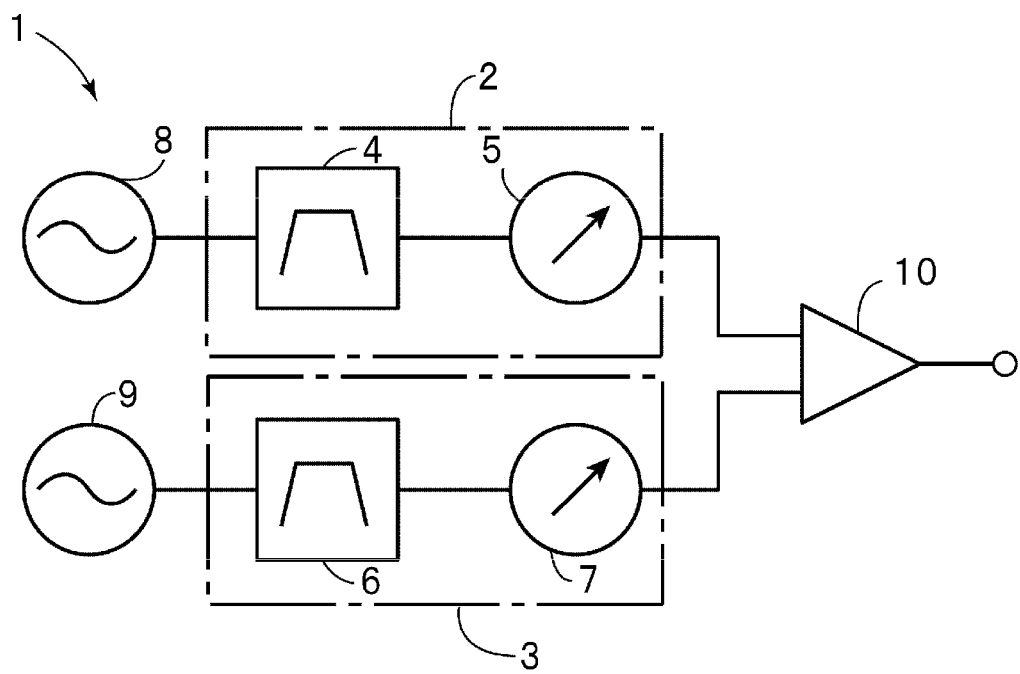
FIG. 1 is a block diagram for describing a sensor for detecting a substance in liquid according to a first preferred embodiment of the present invention.

FIG. 1 is a block diagram that illustrates a circuit configuration of a sensor for detecting a substance in liquid according to a preferred embodiment of the present invention.

As illustrated in FIG. 1, the sensor 1 for detecting a substance in liquid includes a sensing circuit 2 and a reference circuit 3. The sensing circuit 2 includes a sensing SAW element 4 that is connected to a first output-level detecting circuit 5. The reference circuit 3 includes a reference SAW element 6 that is connected to a second output-level detecting circuit 7.

Figure 2:
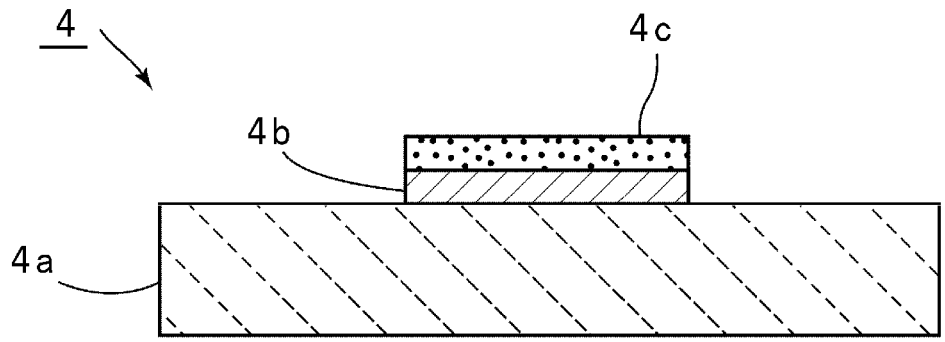
FIG. 2 is a cross-sectional view that schematically illustrates a configuration of a sensing SAW element.
Figure 3:
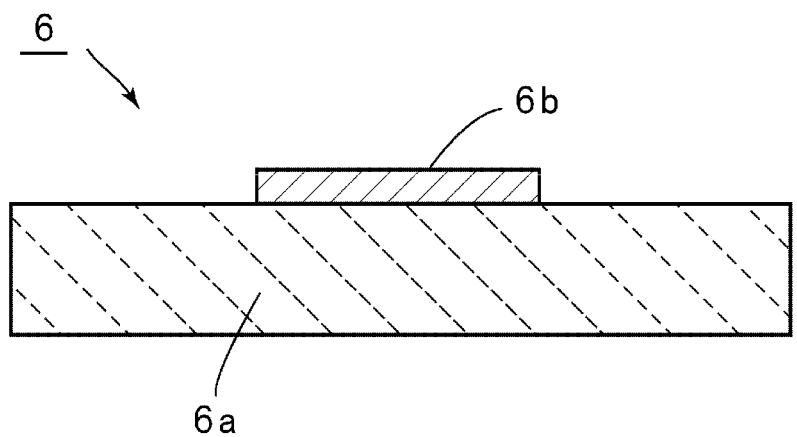
FIG. 3 is a cross-sectional view that schematically illustrates a configuration of a reference SAW element.

Each of the sensing SAW element 4 and the reference SAW element 6 may preferably be defined by a SAW element in which an IDT is provided on a piezoelectric substrate, for example. As schematically illustrated in FIG. 2, in the sensing SAW element 4, an IDT 4b is provided on the upper surface of a piezoelectric substrate 4a, and a reaction film 4c is arranged so as to cover the IDT 4b. In the reference SAW element 6, as schematically illustrated in FIG. 3, an IDT 6b is provided on a piezoelectric substrate 6a. The reference SAW element does not include a reaction film 4c.

When the sensing SAW element 4 is arranged to come into contact with liquid including a detection-target substance, the reaction film 4c reacts with the detection-target substance, and the protein, for example, is coupled to the reaction film 4c. As a result, a mass on the IDT 4b is increased. By utilizing the increased mass, the presence or absence or the density of the detection-target substance can be measured.

The reaction film 4c is preferably made of a suitable material that reacts with a detection-target substance in liquid, for example. For example, to measure an antigen or antibody in liquid, a film in which the antigen or antibody is immobilized may preferably be used as the reaction film. In this case, the antigen or antibody in liquid is coupled to the antigen or antibody immobilized in the reaction film, and an immune complex is formed. This formation changes a mass on the portion in which the IDT is disposed. Such a reaction film made of a suitable material that reacts with a detection-target substance in liquid and changes a mass on the portion in which the IDT is disposed may preferably be selected as the reaction film 4c depending on the properties of the detection-target substance. The detection-target substance is not limited to an antigen and antibody and can be various biochemical materials, including a protein. In addition, the detection-target substance is not limited to such biochemical materials. Various elements and inorganic compounds can also be a target material to be detected. That is, the sensor for detecting a substance in liquid according to preferred embodiments of the present invention is suitably used as a biosensor for detecting a biogenic substance, such as an antigen, antibody, or protein. However, it is not limited to use as a biosensor, and can be used as a device for detecting various substances, for example, a gas sensor.

To remove noise caused by changes in temperature, the reference circuit 3 including the reference SAW element 6 is also used. That is, background noise and noise caused by a change in temperature are removed by subtracting a result obtained in the reference circuit 3 from a result obtained in the sensing circuit 2. Accordingly, the presence or absence and the density of a detection-target substance can be accurately detected.

The first output-level detecting circuit 5 and the second output-level detecting circuit 7 detect an amplitude level as an output of the sensing SAW element 4 and an amplitude level as an output of the reference SAW element 6. The sensing SAW element 4 is connected to a first signal source 8. That is, the first signal source 8 is connected to the sensing SAW element 4 such that a first frequency signal is supplied from the first signal source 8 to the sensing SAW element 4. The sensing SAW element 4 is driven by the first frequency signal.

The reference SAW element 6 is connected to a second signal source 9. The second signal source 9 outputs a second frequency signal having a frequency different from that of the first frequency signal. The reference SAW element 6 is driven by the second frequency signal.

The output terminal of the first output-level detecting circuit 5 is connected to a first input terminal of a differential amplifier 10. The output terminal of the second output-level detecting circuit 7 is connected to a second input terminal of the differential amplifier 10. The differential amplifier 10 detects a difference between an output of the first output-level detecting circuit 5 and that of the second output-level detecting circuit 7, i.e., dp=Pr−Ps, where Ps is the level of an output of the first output-level detecting circuit 5, and Pr is the level of an output of the second output-level detecting circuit 7. That is, in the present preferred embodiment, the first signal source 8 driving the sensing circuit 2 and the second signal source 9 driving the reference circuit 3 are independently provided. To set a driving frequency for the sensing SAW element 4 and that for the reference SAW element 6 to be different from one another, the first frequency signal output from the first signal source 8 and the second frequency signal output from the second signal source 9 are set to be different from one another.

In the present preferred embodiment, the sensing SAW element 4 and the reference SAW element 6 are preferably directly driven by the first signal source 8 and the second signal source 9, respectively, so as to output predetermined frequency signals. That is, because no oscillation circuit is provided, a malfunction and a decrease in sensitivity caused by the coupling of oscillations are not produced. Accordingly, a substance in liquid can be detected with greater sensitivity and greater precision.

Figure 4:
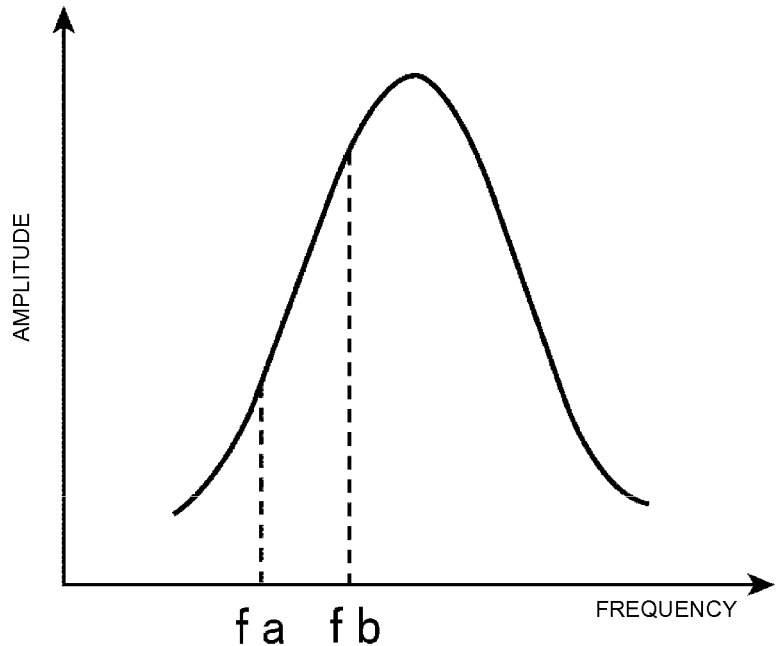
FIG. 4 illustrates a frequency characteristic of an output of a SAW element.
Figure 5A:
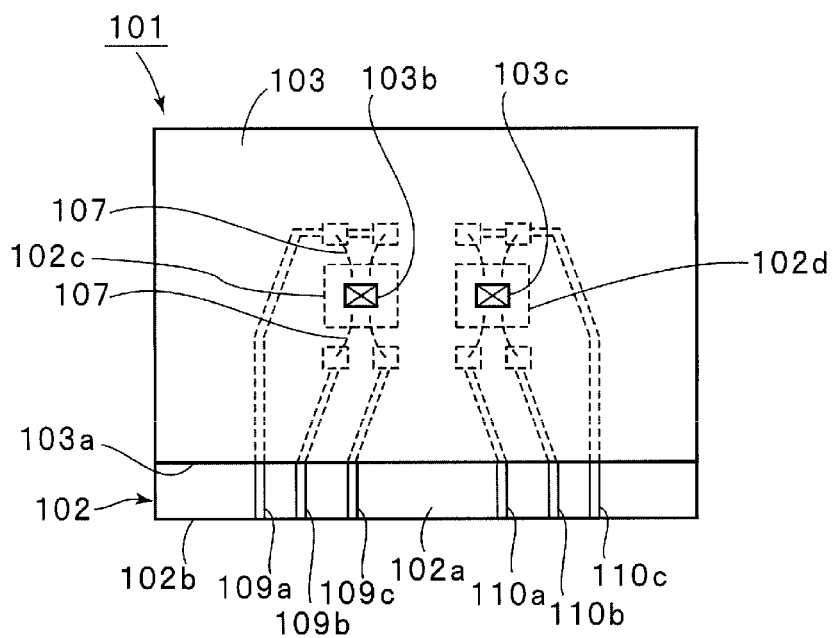
FIG. 5A is a plan view that illustrates one example of a known sensor for detecting a substance in liquid.
Figure 5B:
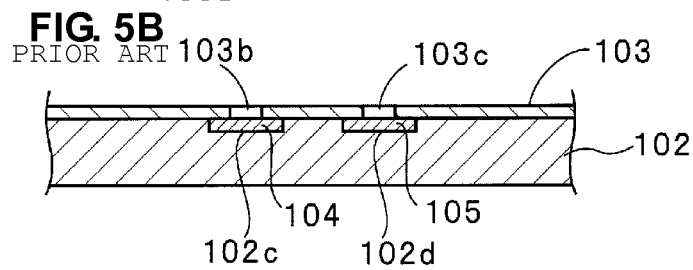
FIG. 5B is a front cross-sectional view that illustrates a main portion thereof.

A measurement principle according to the present preferred embodiment will now be described. When a frequency of a specific signal is input to a SAW element, the output has a frequency distribution, as illustrated in FIG. 4. When a detection-target substance is coupled to the reaction film in the sensing SAW element, a mass on the portion in which the IDT is disposed in the sensing SAW element is increased. This increased mass changes the speed of sound and the frequency in the sensing SAW element. As a result, as illustrated in FIG. 4, the amplitude level is changed by the change in the frequency. This change of the amplitude level, i.e., the change of the amplitude level as the output of the sensing SAW element enables the presence or absence or the density of the detection-target substance to be accurately detected. In addition, in the present preferred embodiment, where the amplitude level as the output of the reference SAW element is Pr and the output as the amplitude of the sensing SAW element is Ps, the differential amplifier 10 outputs the differential output dP=Pr−Ps. By using the value of the dP, the presence or absence or the density of the detection-target substance in liquid can be detected with greater precision.

In the present preferred embodiment, the first frequency signal and the second frequency signal are preferably different from one another, as described above. This will be described with reference to FIG. 4. As illustrated in FIG. 4, the amplitude level at a frequency fa and the amplitude level at a frequency fb are different from one another.

That is, the frequency fa is preferably selected as the first frequency signal output from the first signal source 8, and the frequency fb is preferably selected as the second frequency signal output from the second signal source 9, for example. In this case, the sensing SAW element 4 is driven by the first frequency signal at the frequency fa, and the reference SAW element 6 is driven by the second frequency signal at the frequency fb.

Accordingly, the level of the output detected by the first output-level detecting circuit 5 and that by the second output-level detecting circuit 7 are different from one another in an initial state. In the present preferred embodiment, the first frequency signal and the second frequency signal are selected such that the differential output dP≥0 is satisfied. Accordingly, the first frequency signal and the second frequency signal are selected such that, when a detection-target substance in liquid is coupled to the reaction film and the mass is increased, the amplitude of the sensing SAW element 4 is reduced.

In other words, because the frequency of the first frequency signal is less than a frequency at which the amplitude is a maximum value in FIG. 4, when the detection-target substance in liquid is coupled to the reaction film and the mass is increased, dP can be reliably increased. Thus, the detection-target substance can be detected with greater sensitivity.

It is not necessary to select the first frequency signal and the second frequency signal such that dP≥0 is satisfied. That is, dP≥0 may be satisfied by selecting the frequency difference between the first and second frequency signals, and the substance in liquid can be detected with greater precision.

The first output-level detecting circuit 5 and the second output-level detecting circuit 7 are provided in the preferred embodiment described above. However, neither the first output-level detecting circuit 5 nor the second output-level detecting circuit 7 may be provided. Alternatively, the output of the sensing SAW element 4 and that of reference SAW element 6 may preferably be supplied directly to the differential amplifier 10.

The piezoelectric substrate for a SAW element used in the preferred embodiment described above is not limited to a particular piezoelectric substrate. For example, a suitable piezoelectric single crystal, such as a $LiTaO_3$ substrate, or a lithium niobate ($LiNbO_3$) substrate, or piezoelectric ceramic can be used. Preferably, a 30° to 40° rotated Y-plate X-propagation $LiTaO_3$ substrate may be used, for example. In this case, the detection-target substance in liquid can be detected with greater sensitivity.

The SAW elements 4 and 6 used in the preferred embodiment described above are not limited to a particular SAW element. SAW elements that utilize various types of surface acoustic waves, such as Rayleigh waves or shear-horizontal (SH) waves, for example, can preferably be used. If surface acoustic waves primarily including SH waves are used, an end-surface-reflection SAW device can be provided. As a result, the size of the sensor for detecting a substance in liquid can be reduced.

Each of the SAW elements described above can also be a SAW resonator or a SAW filter.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A sensor for detecting a substance in liquid, the sensor comprising:
   a sensing circuit including a sensing surface acoustic wave element and a first output-level detecting circuit directly connected to the sensing surface acoustic wave element, the sensing surface acoustic wave element including a piezoelectric substrate, an interdigital transducer disposed on the piezoelectric substrate, and a sensing portion in which a reaction film is arranged so as to cover the interdigital transducer and react with a detection-target substance in liquid, and the first output-level detecting circuit being arranged to detect an amplitude level as an output of the sensing surface acoustic wave element;

a reference circuit including a reference surface acoustic wave element and a second output-level detecting circuit directly connected to the reference surface acoustic wave element, the reference surface acoustic wave element including a piezoelectric substrate and an interdigital transducer disposed on the piezoelectric substrate and having no reaction film arranged so as to cover the interdigital transducer, and the second output-level detecting circuit being arranged to detect an amplitude level as an output of the reference surface acoustic wave element;

a first signal source directly connected to the sensing surface acoustic wave element and arranged to generate and supply a first frequency signal having a first frequency to the sensing surface acoustic wave element so as to drive the sensing circuit at a first driving frequency;

a second signal source directly connected to the reference surface acoustic wave element, arranged to generate and supply a second frequency signal having a second frequency that is different from the first frequency to the reference surface acoustic wave element so as to drive the reference circuit at a second driving frequency that is different from the first driving frequency, and being provided independently of the first signal source such that the first signal source and the second signal source are separate and distinct circuit elements; and a differential circuit including a first input terminal connected to an output terminal of the first output-level detecting circuit of the sensing circuit and a second input terminal connected to an output terminal of the second output-level detecting circuit of the reference circuit and arranged to output a differential output that indicates a difference between an amplitude level output from the output terminal of the first output-level detecting circuit of the sensing circuit and an amplitude level output from the output terminal of the second output-level detecting circuit of the reference circuit; wherein the first frequency of the first frequency signal generated and supplied by the first signal source is less than a frequency at which an amplitude of the first frequency signal is a maximum value; and the second frequency of the second frequency signal generated and supplied by the second signal source is less than a frequency at which an amplitude of the second frequency signal is a maximum value.

2. The sensor for detecting a substance in liquid according to claim 1, wherein the first and second frequency signals are selected so as to satisfy $dP \geq 0$, where $dP=Pr-Ps$, and where $Ps$ is an output signal of the sensing circuit, $Pr$ is an output signal of the reference circuit, and $dP$ is an output signal of the differential circuit.

3. The sensor for detecting a substance in liquid according to claim 1, wherein each of the piezoelectric substrates is a 30° to 40° rotated Y-plate X-propagation lithium tantalate substrate.

4. The sensor for detecting a substance in liquid according to claim 1, wherein each of the sensing surface acoustic wave element and the reference surface acoustic wave element is a surface acoustic wave element that utilizes surface acoustic waves primarily including shear-horizontal waves.

* * * * *